United States Patent
Cottrell

(10) Patent No.: US 9,271,812 B2
(45) Date of Patent: *Mar. 1, 2016

(54) MODIFIED DENTAL IMPLANT FIXTURE

(75) Inventor: Richard Cottrell, Lake Forest, IL (US)

(73) Assignee: DENTSPLY International Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/890,519

(22) Filed: Aug. 7, 2007

(65) Prior Publication Data

US 2007/0281281 A1   Dec. 6, 2007

Related U.S. Application Data

(63) Continuation of application No. 10/752,189, filed on Jan. 5, 2004, now Pat. No. 7,270,542, which is a continuation of application No. 10/223,773, filed on Aug. 19, 2002, now Pat. No. 6,672,872, which is a continuation-in-part of application No. 10/011,866, filed on Dec. 3, 2001, now Pat. No. 6,655,961.

(51) Int. Cl.
*A61C 13/00* (2006.01)
*A61C 8/00* (2006.01)

(52) U.S. Cl.
CPC ............ *A61C 8/005* (2013.01); *A61C 8/0018* (2013.01); *A61C 8/0025* (2013.01);
(Continued)

(58) Field of Classification Search
CPC ........ A61C 8/00; A61C 8/001; A61C 8/0006; A61C 8/0019; A61C 8/0033; A61C 8/0056; A61C 8/0004; A61C 8/0022; A61C 8/0024; A61C 8/0025; A61C 8/0027; A61C 8/0031; A61C 8/0034; A61C 8/0039; A61C 8/0037; A61C 8/004; A61C 8/0042; A61C 8/0043; A61C 8/0045; A61C 8/005; A61C 8/0069; A61C 8/0071; A61C 8/0072; A61C 8/0074; A61C 8/0075; A61C 8/0077; A61C 8/0078; A61C 8/0083
USPC ........................................ 433/172–176, 201.1
See application file for complete search history.

(56) References Cited

U.S. PATENT DOCUMENTS 5,009,596 A * 4/1991 Soderberg ............... 433/173
5,030,095 A   7/1991 Niznick
(Continued)

FOREIGN PATENT DOCUMENTS

DE  19931701 A1 * 1/2001
FR  2737847    * 2/1997
(Continued)

OTHER PUBLICATIONS provisional application 60311089, Abarno, Juan.*
(Continued)

*Primary Examiner* — Yogesh Patel
(74) *Attorney, Agent, or Firm* — David A. Zdurne; Douglas J. Hura; Leana Levin

(57) ABSTRACT

A modified dental implant fixture designed to preserve lingual bone by having the coronal aspect of the implant being compatible with bony anatomy that is higher on the lingual side of the implant surgical site. The implant may be of either the single stage or the two stage design. By modifying the shape of the top of the implant fixture to mimic healing/healed bony anatomy, bone is preserved and bone growth is possibly encourage.

10 Claims, 6 Drawing Sheets

(52) U.S. Cl.
CPC ............ *A61C 8/0075* (2013.01); *A61C 8/0077* (2013.01); *A61C 8/006* (2013.01); *A61C 8/0069* (2013.01); *A61C 8/0078* (2013.01)

(56) References Cited

U.S. PATENT DOCUMENTS

| | | | |
|---|---|---|---|
| 5,078,606 A | | 1/1992 | Soderberg |
| 5,102,336 A | * | 4/1992 | Linkow ............ 433/176 |
| 5,312,255 A | | 5/1994 | Bauer |
| 5,362,236 A | | 11/1994 | Branemark |
| 5,417,568 A | | 5/1995 | Giglio |
| 5,503,558 A | | 4/1996 | Clokie |
| 5,564,925 A | | 10/1996 | Shampanier |
| 5,564,926 A | * | 10/1996 | Branemark ............ 433/174 |
| 5,588,838 A | * | 12/1996 | Hansson et al. ............ 433/173 |
| 5,591,029 A | | 1/1997 | Zuest |
| 5,674,072 A | | 10/1997 | Moser et al. |
| 5,702,695 A | | 12/1997 | Clokie |
| 5,759,034 A | * | 6/1998 | Daftary ............ 433/173 |
| 5,779,480 A | * | 7/1998 | Groll et al. ............ 433/173 |
| 5,785,525 A | | 7/1998 | Weissman |
| 5,810,592 A | * | 9/1998 | Daftary ............ 433/173 |
| 5,863,200 A | * | 1/1999 | Hamada et al. ............ 433/173 |
| 5,863,201 A | | 1/1999 | Lazzara et al. |
| 5,879,161 A | | 3/1999 | Lazzara |
| 5,890,902 A | | 4/1999 | Sapian |
| 5,947,735 A | | 9/1999 | Day |
| 6,164,969 A | | 12/2000 | Dinkelacker |
| 6,217,333 B1 | | 4/2001 | Ercoli |
| 6,261,097 B1 | * | 7/2001 | Schmutz et al. ............ 433/173 |
| 6,283,754 B1 | | 9/2001 | Wohrle |
| 6,547,564 B1 | | 4/2003 | Hansson |
| 6,733,292 B2 | * | 5/2004 | Odrich et al. ............ 433/173 |
| 6,854,972 B1 | | 2/2005 | Elian |
| 2003/0031982 A1 | * | 2/2003 | Abarno ............ 433/173 |
| 2003/0228555 A1 | | 12/2003 | Morgan et al. |

FOREIGN PATENT DOCUMENTS

| | | |
|---|---|---|
| WO | WO 01/49199 A | 7/2001 |
| WO | WO 01/50972 A | 7/2001 |

OTHER PUBLICATIONS

Cawood, J.I. and Howell, R.A., "Reconstructive Preprosthetic Surgery," 1 Anatomical Considerations, Int'l Journal Oral Maxillofacial Surgery, 1991: 20, 75-82.

Niznick, Gerald, "The Core-Vent Implant System," The Journal of Oral Implantology, vol. 10, No. 3, 1982.

* cited by examiner

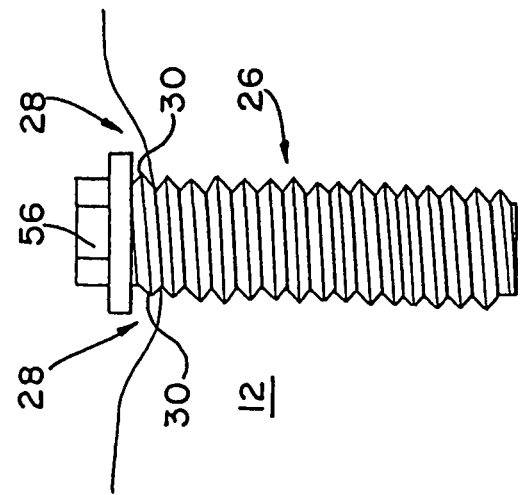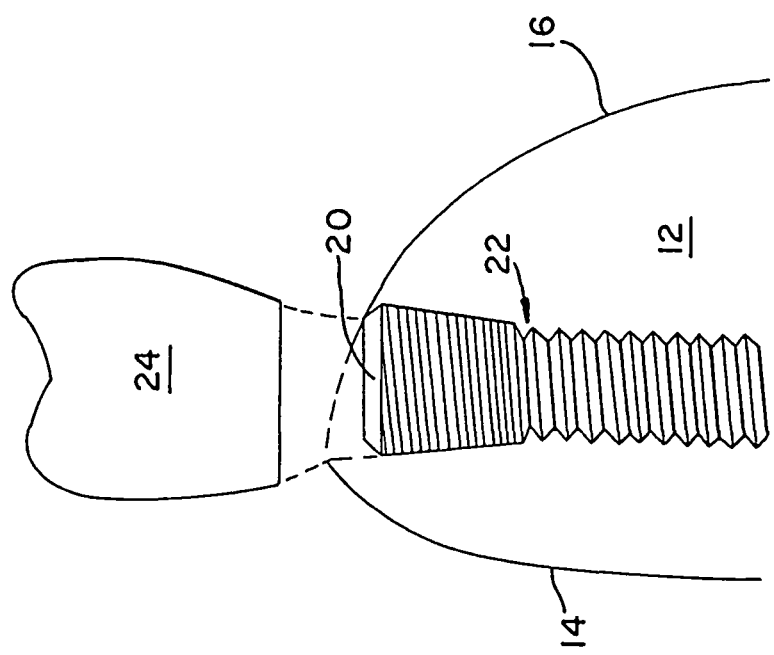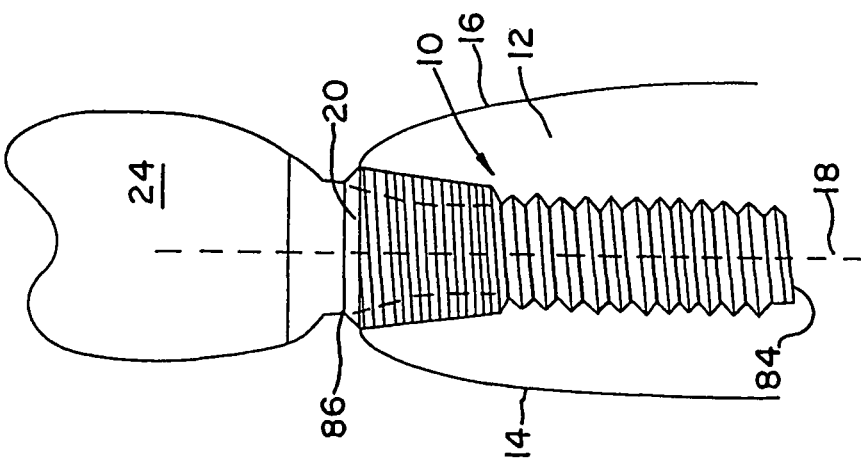

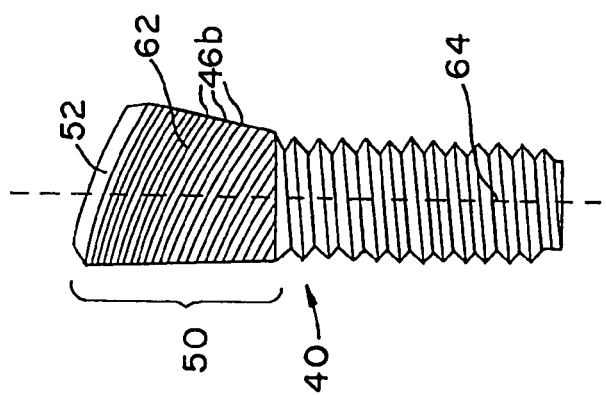
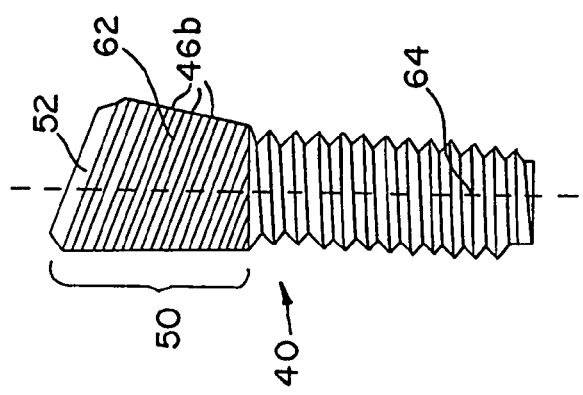
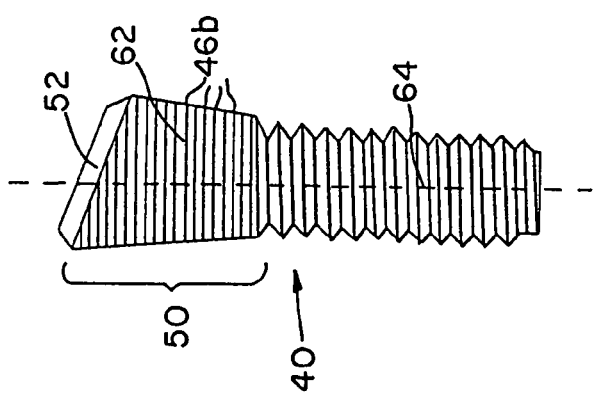
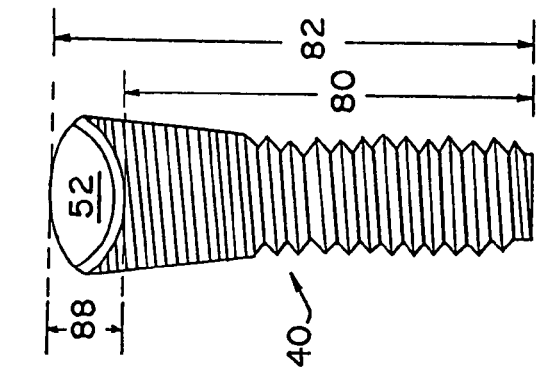

MODIFIED DENTAL IMPLANT FIXTURE

CROSS-REFERENCE TO RELATED APPLICATION

This application is a continuation application of U.S. application Ser. No. 10/752,189, filed on Jan. 5, 2004, now U.S. Pat. No. 7,270,542 which is a continuation of U.S. application Ser. No. 10/223,773, filed Aug. 19, 2002, now U.S. Pat. No. 6,672,872, issued on Jan. 6, 2004, which is a continuation-in-part application, and, therefore, claims the benefit under 35 U.S.C. §120, of U.S. patent application Ser. No. 10/011,866 filed Dec. 3, 2001, now U.S. Pat. No. 6,655,961, issued on Dec. 2, 2003, the entire contents of which are incorporated herein by reference.

BACKGROUND OF THE INVENTION

The present invention relates generally to dental implants, and more specifically to a dental implant having an improved configuration to take advantage of the bone topography that is often present following tooth extraction.

Dental implants are used in place of missing and/or extracted natural teeth as the base of support for an abutment and final prosthesis in the attempt to restore normal oral function. Once teeth have been extracted, the alveolar bone at the extraction site heals and begins to undergo resorption. The resorption process is halted by restoring loading forces with a dental implant. The topographic changes of the alveolar bone have been described in the dental literature and are time dependent with regard to the amount of bone resorption. While implants are designed to replace natural teeth, they must also be designed to consider the phenomenon of how bone heals and remodels following tooth extraction.

The implant body is surgically inserted in the patients jaw and becomes integrated with the bone. More specifically, the implant body is screwed or pressed into holes drilled in the respective bone. The surface of the implant body is characterized by macroscopic and microscopic features that aid in the process of osseointegration. Once the implant is fully integrated with the jaw bone, the abutment is ready to be mounted. For two-stage implant designs, the abutment passes through the soft tissue that covers the coronal end of the implant after healing and acts as the mounting feature for the prosthetic device to be used to restore oral function. Implants of the single-stage design extend through the tissue at the time of surgical insertion. The coronal end of the implant body acts as part of a built-in abutment design with the margin of the coronal collar usually used as the margin for the attachment of the prosthesis used to restore oral function. These components, the implant and abutment, are typically fabricated from titanium or an alloy of titanium as well as zirconia based, alumina based or sapphire based ceramics. In some instances, ceramics and metals are combined to make a single component, though this is usually limited to the abutment component of the implant system.

One of the major problems associated with dental implants stems from the failure to provide for the ideal alignment of implant fixtures in bone. Misalignment often results in the implant being positioned lingual to the ideal placement. Loosening or fracture of the abutments and even the implant body can result due to the adverse forces involved. Restorative dentists complain that the implants are not properly aligned by the surgeons, and the surgeons complain that the restorative dentists do not understand the challenges associated with the alignment process.

One of the most commonly placed fixture designs is the Branemark type implant. These implants are ideally positioned in the approximate center line of the space where the extracted tooth was previously positioned. As with most traditionally designed implants, the Branemark type fixture relies on a flat surface perpendicular to the long axis of the implant body for strength when joining the implant and the abutment together. This design usually displays a bone loss pattern described as a cupping of the bone at the coronal end of the implant once loaded with occlusal forces. This cupping pattern usually stabilizes after about one year of function with vertical bone loss of approximately 2 mm but, by that time, loss of bone critical to the predictable support of overlying soft tissue is lost.

Other implant systems often used are of the so called Astra Tech and ITI Straumann type implants. These implant designs have an internal conical connector and do not rely on perpendicular orientation of a flat surface for strength at the implant/abutment interface. Astra implants, due to or in combination with the rigid conical abutment connection and the presence of coronal stress reducing micro threads on the implant body, greatly reduce, and in some instances do not display the aforementioned bone loss patterns. However, the problem still exists as to the misalignment of such implants due to the flat topped coronal feature of the implant body in its present configuration.

Astra Tech has addressed coronal bone loss by introducing micro threads at the coronal portion of the implant body to distribute forces transferred to the surrounding bone. Other attempts to enhance implant designs have addressed bone loss patterns and lack of soft tissue support by focusing on the coronal aspect of the implant body in hopes of mimicking natural CEJ (cemento-enamel junction) anatomy or shaping the implant body to be more root like in character. Implants duplicating tooth anatomy in some way, shape or form have not had the same level of success as the Astra Tech concept. Unfortunately, once the tooth has been extracted, the bone does not remember what the tooth looked like, or what function it provided. Implants must be designed as dental implants, not morphic copies of teeth. Even with the Astra's success, the design of the implant fixture and how that design interacts with the bony anatomy at the surgical site has not been addressed correctly. To date, no design has considered the anatomy of how bone heals in the human jaw following tooth extraction.

Accordingly, it is a general object of the present invention to provide an improved implant such that many of the problems related to implant placement are eliminated.

It is another general object of the present invention to incorporate design features that take advantage of how bone heals.

It is a more specific object of the present invention to enable implants to be placed in surgical sites of sloping bony anatomy more precisely and predictably.

Another object of the present invention is to preserve lingual bone by having the coronal aspect of the implant being compatible with the bony anatomy that is higher on the lingual side of the surgical site.

It is another object of the present invention to provide for increased strength of the implant/abutment system.

Yet another object of the present invention is to reduce the amount of time required by the restorative dentist to prepare and idealize the abutment.

Another object of the present invention is to reduce the number of abutment orientation surfaces, thereby reducing the size requirement for the implant body.

Still another object of the present invention is to make the use of snap on impression caps more useful and resulting in the final prosthesis being more functional and cosmetic in appearance.

Yet another object of the present invention is to allow for a single implant to be placed in the anterior region of the human jaw with predictable soft tissue contours supported by bone.

Still another object of the present invention is to allow multiple implants to be placed more predictably next to one another in the anterior region of the human jaw.

Another object of the present invention is to combine the two-stage implant design having a length greatest on the lingual side of the jaw with an internal conical connection.

Still another object of the present invention is to modify the design of single stage implants to have features that enhance placement in sloping bony anatomy.

These and other objects, features and advantages of the present invention will be clearly understood through a consideration of the following detailed description.

SUMMARY OF THE INVENTION

According to the present invention, there is provided a dental implant for implanting within a human jawbone, the jawbone having lingual and buccal sides. The implant includes a generally cylindrical longitudinal body with an outer surface, an apical end and a coronal end. An abutment having a lower portion for connecting with the body. The coronal end is contoured such that when the implant is positioned within the jawbone the length between ends of the body is greatest within the lingual third of the jawbone.

BRIEF DESCRIPTION OF THE DRAWINGS

The features of the present invention, which are believed to be novel, are set forth with particularity in the appended claims. The invention, together with the further objects and advantages thereof, may best be understood by reference to the following descriptions take in conjunction with the accompanying drawings, in the several figures of which like reference numerals identify like elements, and in which:

FIG. 1 is a side view of the ideal implant placement within the jaw bone.

FIG. 2 is a side view of the ideal alignment of a typical implant buried within the jaw bone with sloping topographic anatomy to avoid fixture thread exposure.

FIG. 3 is a front view of a Branemark type implant design showing typical cupping bone loss at the coronal aspect of the implant after loading with functional forces.

FIG. 9 is an elevated front view of the preferred embodiment of the implant of the present invention.

FIGS. 10-12 are elevated side views of similar embodiments of the present invention.

DESCRIPTION OF THE PREFERRED EMBODIMENT

Figure 4:
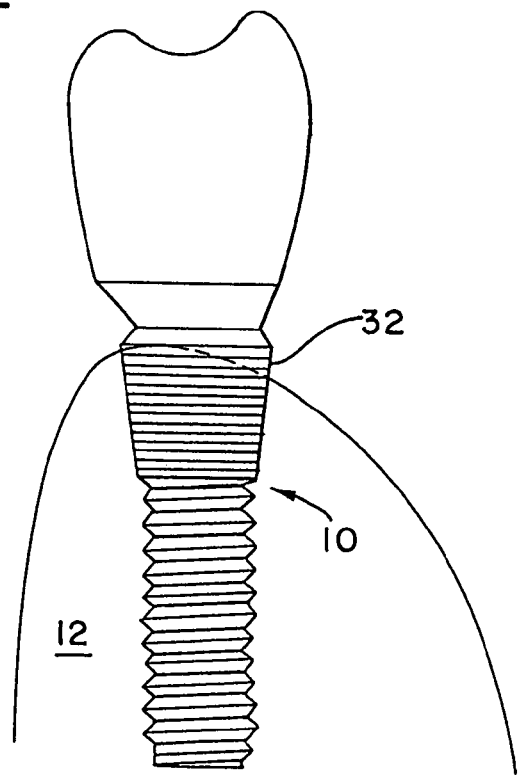
FIG. 4 is a side view of the ideal alignment of a typical implant within the jaw bone with sloping topographic anatomy having threads exposed on the facial aspect of the implant body.

Dental implants are used in place of missing and/or extracted natural teeth as the base of support for an abutment and final prosthesis in the attempt to restore normal oral function. Once a tooth has been extracted, the bone from which the tooth originated heals and is forever changed and probably continuously changing due to the forces exerted on it. Dental implants need to be designed to take into account the natural healing process of bone.

Referring now to the Figures, and in particular FIG. 1, a typical implant 10 is illustrated implanted within the jaw bone 12. For purposed of describing the invention, the bone 12 of the human jaw will primarily be discussed with respect to its lingual 14 and buccal 16 sides. This bone 12 illustrated by FIG. 1 is that of an ideal, but infrequent implant site. That is, lingual side 14 and buccal side 16 bone appear to be comparable in height and shape with respect to the center 18 of the maximum height of available bone. Therefore, the typical implant 10, with its flat top or coronal aspect 20 is suitable for its intended purpose when implanted within such a jaw bone condition.

However, when teeth are extracted, this ideal bone site of FIG. 1 is seen more frequently in drawings from implant manufacturers rather than at the actual surgical sites encountered during surgical placement of implant fixtures. This is because the bone does not heal evenly once a tooth has been extracted. It has been found that bone heals based on the principles of bone biology and surrounding bony anatomy, surrounding bony and soft tissue anatomy as well as blood supply to the area. To a degree, bone healing and/or remodeling is influenced by the placement and subsequent loading of an implant fixture in the area of the extracted tooth or teeth. A number of studies have been conducted regarding bone loss patterns following tooth loss. One such outstanding study, by Cawood and Howell was published in the *International Journal of Oral and Maxillofacial Surgery* in 1991.

This study analyzed patterns of alveolar bone resorption from a sample of 300 dried skulls with edentulous jaws. In general, bone loss is four times greater in mandible than the maxilla. One can construe from this study that the highest point of bone anatomy is at the lingual side of extracted teeth after healing for a time period even as short as several months. Due to the natural bony contours in the anterior area of the upper and lower jaws, this healing pattern, often referred to as facial collapse of bone, is more immediate than in the posterior upper and lower jaws. If an implant fixture is placed in the center of the maximum height of available bone, the implant can end up too far to the lingual from the point of view of the restorative dentist.

To avoid this overly lingual placement, implants can be submerged even to the facial level of bone. FIG. 2 is illustrative of such a submersion as the implant 22 is shown with its coronal aspect 20 fully submerged on the lingual side 14 and even with the bone 12 on the buccal side 16. The crown 24 to be attached to the abutment is then affixed to the coronal aspect 20 in an attempt to restore normal oral function. As such an implant needs to be buried within the bone to compensate for the shape of the healing bone, the implant 22 must be significantly shorter in length than the ideal size shown in FIG. 1. This results in a weaker and less stable implant/abutment complex.

Another problem with burying implants is illustrated by FIG. 3. This Figure shows a typical Branemark type implant 26 which was previously buried within the bone 12 as discussed above. After the implant has been affixed with an abutment and crown, the loading forces typically produce a bone loss pattern referred to as cupping 28. This bone loss usually exposes the threads 30, and, essentially, results in the placement of what amounts to be a shorter implant and thus a weaker implant in the jaw bone.

Another way to avoid overly lingual implant placement is illustrated by FIG. 4. Here, the implant 10 has been inserted into the bone 12 with the proper alignment (as it had in FIG. 2), but now the implant is protruding due to the sloping bony anatomy. Maximum height of available bone was engaged, but exposed threads 32 compromise the ideal facial contour of the final restoration.

Figure 5:
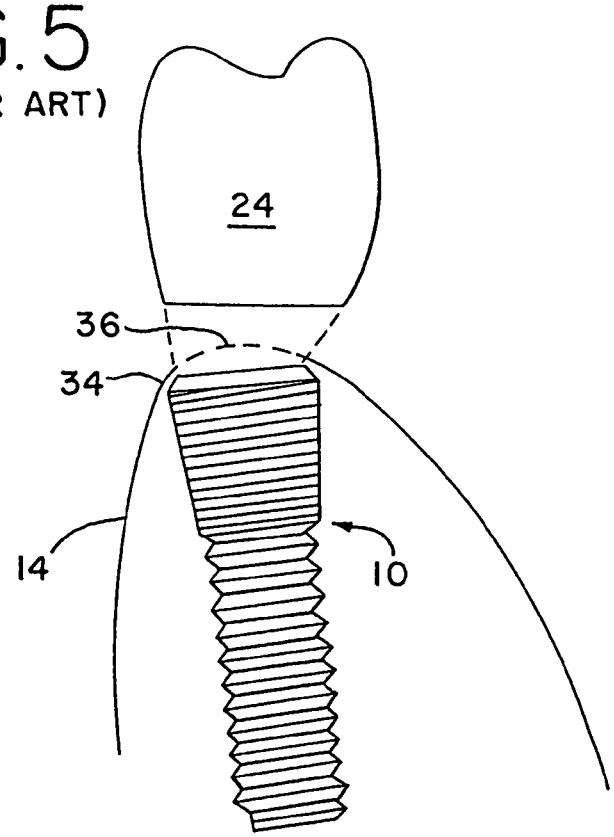
FIG. 5 is a side view of the typical implant placed within the center of the maximum available bone height.

While the positioning of the implant is improved by burying or protruding same, supporting bone is compromised in one instance (FIG. 2) and poor gingival profile results within the other placement (FIG. 4). In an attempt to avoid these problems in the mandible, surgeons may opt to misalign the implant by angling its position as shown in FIG. 5. Here, the implant is angled towards the lingual to avoid perforating the lingual plate of bone 34. In other words, the implant 10 is placed in the middle of the highest point of bone 36 lingual to where the missing tooth was previously positioned. Thus, this kind of positioning may create the greatest problem for the restoring dentist as he now must attempt to esthetically and functionally position the crown 24 and abutment.

Proper alignment of the dental implant is essential to the esthetics as well as the mechanics of proper oral function. If the abutment and crown are affixed to a misaligned implant, the tooth not only looks unattractive, but it will not be able to function properly as unfavorable loading forces will exist. Referring back to FIGS. 1-5, FIG. 1 shows a properly aligned implant 10 and thus a properly aligned crown 24. FIGS. 2 and 4 show proper alignment of the implant, but demonstrate other problems previously described. Finally, FIG. 5 shows an improperly aligned implant and thus a crown affixed to the buccal of the implant fixture.

Figure 15:
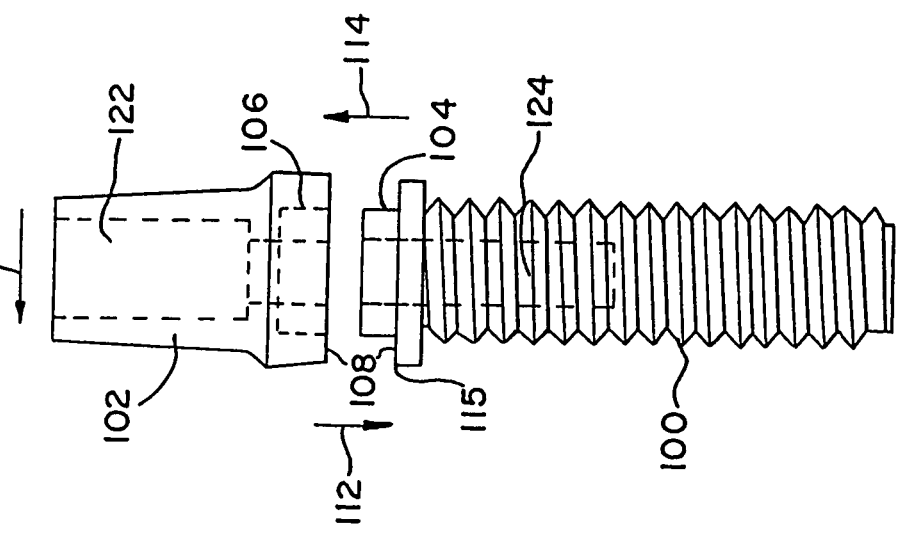
FIG. 15 is a front view of a Branemark type implant and associated abutment design.

Additionally, the type of abutment connection incorporated into the implant design, i.e. the Branemark design of FIG. 3 or the Astra design of FIGS. 1-2 and 4-5, results in implants having decidedly different clinical characteristics. In particular, and referring to FIG. 15, the connection between the implant body 100 and the abutment 102 of a two-stage implant of the Branemark design is characterized by a slip joint connection, using an external hex 104 on the coronal end of the implant in connection with the internal hex 106 of the abutment, and flat matting surfaces 108 between the abutment 102 and the implant 100 which are perpendicular to the long axis of the implant. These flat surfaces limit the joint connection as the parts come together. The slip fit joint typical of the Branemark and other flat matting platform designs result in a tipping action 110 causing loading stress patterns 112 on one side and strain patterns 114 on the other side of the implant body, because the outer edge 115 to the flat platform, 108 acts as a mechanical fulcrum point. It is hypothesized that when this stress/strain on the coronal surface of the implant body is transferred to the surrounding bone, cupping (previously discussed) bone loss occurs.

Figure 16:
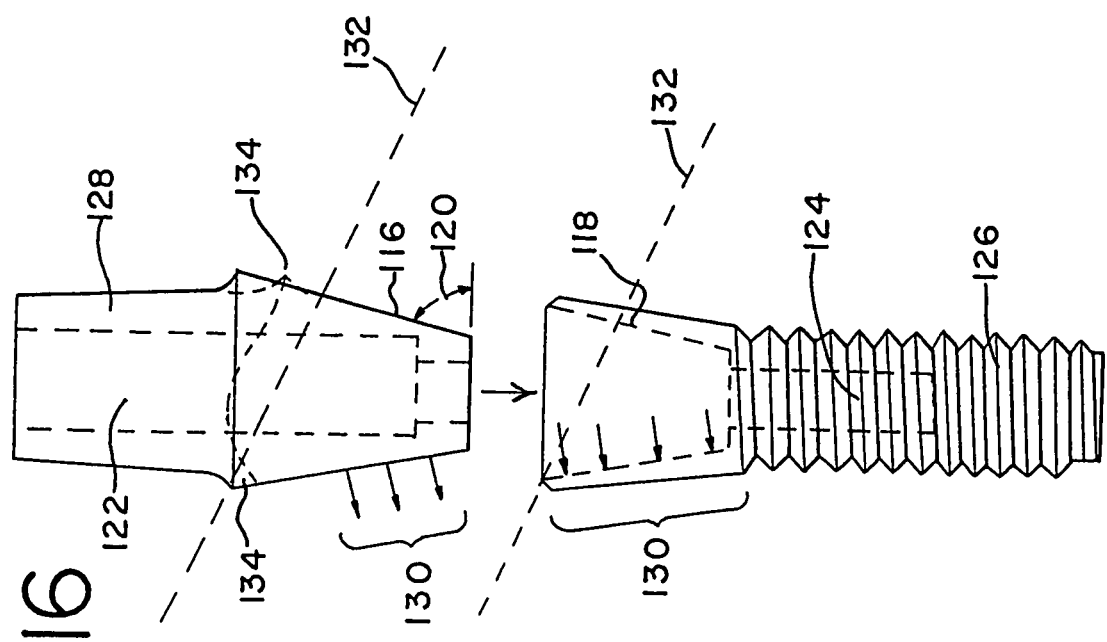
FIG. 16 is a side view of an Astra type implant and preferred embodiment associated abutment design.

By contrast, the Astra-type implant uses what is referred to as a conical connection which is characterized by the male 116 and female 118 cones of FIG. 16. The typical taper 120 for the connection of these coronal extension components range, but are not limited to, from about 5 to 30 degrees. The degree of taper is one factor that determines the extent the two components are swagged together when the connection bolt is threaded through the bolt hole of the abutment 122 and the threaded hole of implant 124 and tightened. The swagged fit becomes a cold weld as far as the implant 126 and the abutment 128 connection are concerned. This eliminates micro movement and distributes the stress/strain far more favorably at the coronal end of the implant body. The matting surfaces of this conical connection need no flat joint limiting surfaces perpendicular to the long axis of the implant body because the male and female mating surfaces and the joint limiting surfaces are one in the same. Upon off axis loading forces this type of abutment-fixture joint distributes stress 130 more evenly within the joint itself avoiding peak loading moments and resulting in a tight and bio-mechanically stable connection.

Since the Astra Tech type implants do not have a flat coronal aspect that is integral to the abutment connection, it is possible to shape the coronal contours to mimic healing/healed bony anatomy at the implant surgical site. Additionally, because Astra Tech implants do not loose coronal bone as do the Branemark type implants, it is possible to preserve and possibly encourage slight bone growth in the coronal direction. By preserving lingual bone height, bone mesial and distal to the implant will also be maintained because, according to studies, including Cawood and Howell, bone slopes apically from the lingual. Preserve the lingual bone, and more bone adjacent to the implant on the mesial and distal sides will be preserved. This is critical if predictable soft tissue papilla overlying these hard tissue sites is to be generated or maintained. It has been shown that only 4 mm of papilla height over mesial and distal bone is considered a level that the restorative dentist can rely on being generated time and again. Without surrounding esthetic papilla, even the most perfectly contoured crown is unsightly in the upper anterior region of the mouth.

Accordingly, the present invention will be described as it relates to the Astra type swagged implant. In particular, the combination of the conical connection and the incorporation of stress distributing micro threads/grooves in the coronal aspect of the implant in addition to surface texturing seem to be the primary design factors preventing "cupping" bone loss from occurring. In its broadest aspects, the design modification of the present invention comprises a revised angle of slope 132 of both the implant and abutment. This revision extends to the abutment contour 134 as well. It will be appreciated that in order for the sloped design modification to be of any value, the problem of "cupping" bone loss must be overcome. The implant design cannot significantly modify the bony topography/anatomy once the implant is loaded. Secondly, the basic design has to be such that it can in fact be modified to incorporate alternate coronal contour to mimic how bone heals following tooth loss. Thus the basic design of the two stage Astra implant allows not only for this modification, but for this modification to be effective.

Figure 6:
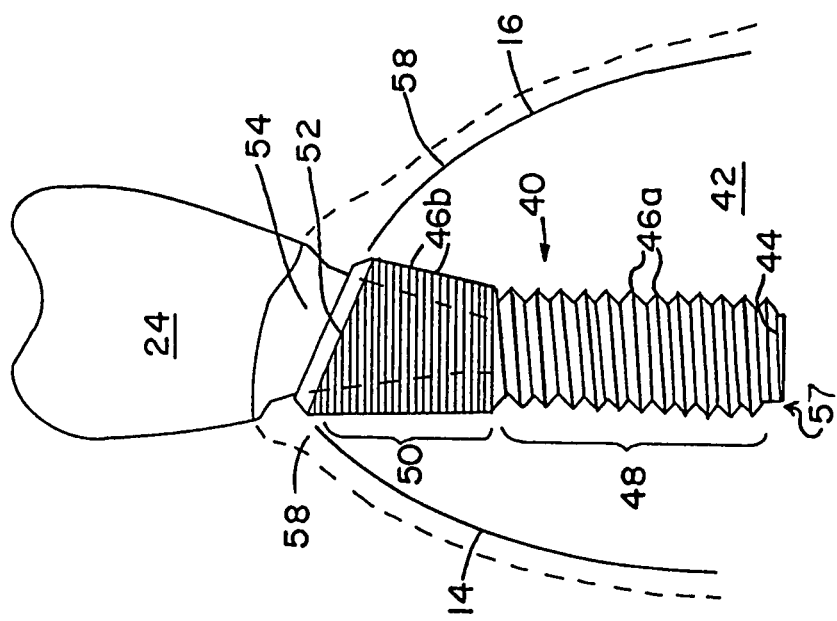
FIG. 6 is a side view of the preferred embodiment of the implant of the present invention.

The preferred embodiment of the present invention is illustrated by FIG. 6. The implant 40 is a cylindrical longitudinal structure designed for bone 42 engagement. The typical length 82 (FIG. 9) of the preferred embodiment is much like the currently used implants. That being between 9 to 18 mm base 84 to top 86 (FIG. 1) while the typical diameter is between 3 to 6.5 mm base 84 to top 86. The body of the implant 40 is preferably, but need not be, comprised of screw threads 46 to aid in the implantation process. The lower (apical) portion 48 of the implant body includes larger threads 46a than the smaller threads 46b of the upper (coronal) portion 50. It has been found that the smaller threads 46b significantly reduce stress forces transmitted to bone and helps to preserve cortical bone. They also increase the fixture strength by adding wall thickness without changing the outer dimension of the implant, compared to larger and deeper threads in the same area of the implant. (These deep threads of current practices tend to dig into the body of the implant and weaken it). However, other means may be used on the outside surface of the implant 40 affixed to the implant within the bone 42, so long as the apical end 44 thereof is securely anchored. The surface of the implant 40 may be textured/coated in differing ways to promote osseointegration.

The coronal end 52 of the implant 40 accepts the base of the prosthetic abutment 54 using connection mechanisms of different designs. An example of such a design is the hex shape 56 shown on the implant 26 of FIG. 3. While the commonly used internal hex or twelve position internal star design can be used, other options are now possible since the implant design has one vs. multiple orientations. Three to five sided abutment alignment surfaces with from three to twelve internal designs are feasible; even one or two alignment surfaces are possible. Reducing the number of abutment orientation surfaces reduces the size requirements for this feature of the implant body. This is important in developing smaller fixtures suitable for use to replace lower anterior teeth.

The basic concept of the present invention is the contouring or sloping of the coronal 52 or top of the implant fixture such that lingual bone 14 is engaged and preserved. This coronal contour can be a straight line or a slightly convex contoured design so long as one bone engaging side 56 of the implant body (which would become the lingually oriented side of the implant fixture) is longer in the apical-coronal bone engaging dimension than any other apical-coronal bone engaging dimension. This apical-coronal dimension or lingual high point does not include any implant collar (if present), but only the bone engaging surface of the implant since the invention primarily addresses bone preservation with predictable soft tissue preservation being understood to be dependent on maintaining underlying supporting bone. Biomechanics are improved for the entire implant 40 abutment 54 and crown 24 complex. Soft tissues 58 are much more predictable since underlying support bone is preserved.

Surgeons will be much less inclined to place fixtures at the middle of the maximum height of available bone which is often to the lingual of the desired implant position (see FIG. 5). The sloping surface of the coronal 52 makes it much more likely that placement in the center of the space formerly occupied by the missing tooth will be possible. Because the lingual aspect of the implant 40 can be placed more coronally without the compromise inherent with flat top designs (See FIGS. 2-5), a more favorable implant fixture to prosthesis ratio results which improves stress distribution. Furthermore, the design of the present invention does not reduce the strength of the implant, but in fact makes it stronger by extending the lingual side of the fixture coronally. The implant fixture, when surgically placed, is longer by the height of the lingual coronal extension, but is not placed deeper in the jaw bone.

Figure 8:
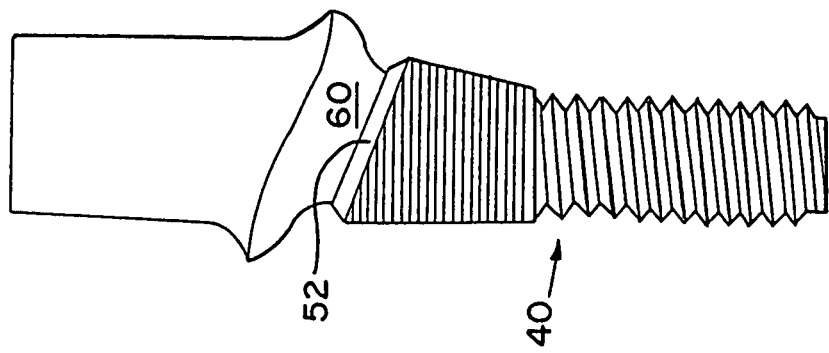
FIG. 8 is an elevated side view of another embodiment of the implant of the present invention with a large sized contoured abutment attached coronally.
Figure 7:
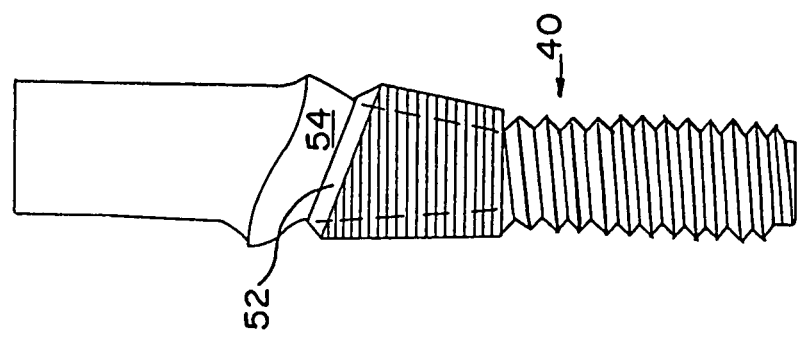
FIG. 7 is an elevated side view of another embodiment of the implant of the present invention with a small sized contoured abutment attached coronally.

Referring now to FIG. 7, the abutment 54 design simulates or follows natural tissue contours 58 because of the coronal sloping 52 feature of the implant. This dramatically reduces the amount of time required by the restorative dentist to prepare and idealize the abutments. Similarly, FIG. 8 shows a contoured abutment 60 of a larger size, which may be more suited for a molar tooth. In any event, the designs of FIGS. 7 and 8, or any similar designs that have tissue or gingival contour to take advantage of the coronal contour of the implant body, will enable the restorative dentist to idealize final margin placement rapidly.

The contouring or sloping of the coronal 52 or top of the implant fixture may best be illustrated by FIG. 9. Here, the differential bone-engaging surface of the implant 40 is shown with respect to its buccal length ($L_1$) 80 in comparison to its lingual length ($L_2$) 82. While the preferred contour may differ from patient to patient, preferably the height differential ($L_2-L_1$) 88 is between 1 and 4 mm, more preferably this differential 88 is between 2 and 3 mm. Therefore, as is shown, the bone-engaging surface, or the outer surface of the implant which is in contact with the jaw, of the implant 40 is longer on one side (lingual) than the other. With such a shape, bone preservation throughout the jaw is achieved.

The coronal end 50 of the implant body 40 is preferably characterized by textured grit blasting 62, (or acid etching, plasma spray technique, etc.) with or without micro threads/grooves 46b as shown in FIG. 10. If micro threads/grooves are evident, they may be perpendicular (FIG. 10) to the long axis 64 of the implant 40, or parallel to the sloped (FIG. 11) or convex (FIG. 12) coronal contour 52. Having the micro threads/grooves 46b parallel to the coronal contour 52 as in FIGS. 11 and 12 may further aid in bone preservation and possibly coronal bone apposition.

Figure 13:
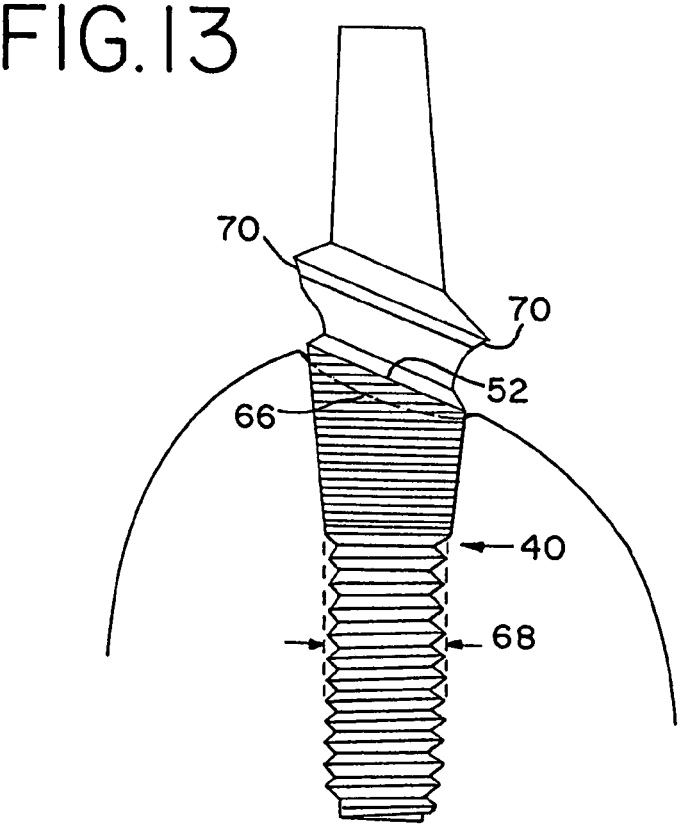
FIG. 13 is a side view of the preferred embodiment of the implant of the present invention of the two stage type design with an abutment designed to be used with snap-on impression caps.

FIG. 13, like FIGS. 6-12, illustrates a design of the present invention as it relates to a two-stage type implant. The body 40 of the implant is widest at the most coronal bone engaging aspect 66 and narrows moving apically before having parallel walls 68 in the apical half of the fixture. This inward coronal feature allows for thicker bone surrounding the implant coronally, while at the same time creating adequate coronal width to resist mechanical occlusal loading. The two-stage design of FIG. 13 takes advantage of the sloped coronal surface 52 and enables the use of a snap-on impression caps. These impression caps engage the undercut 70 of the abutment margins.

Figure 14:
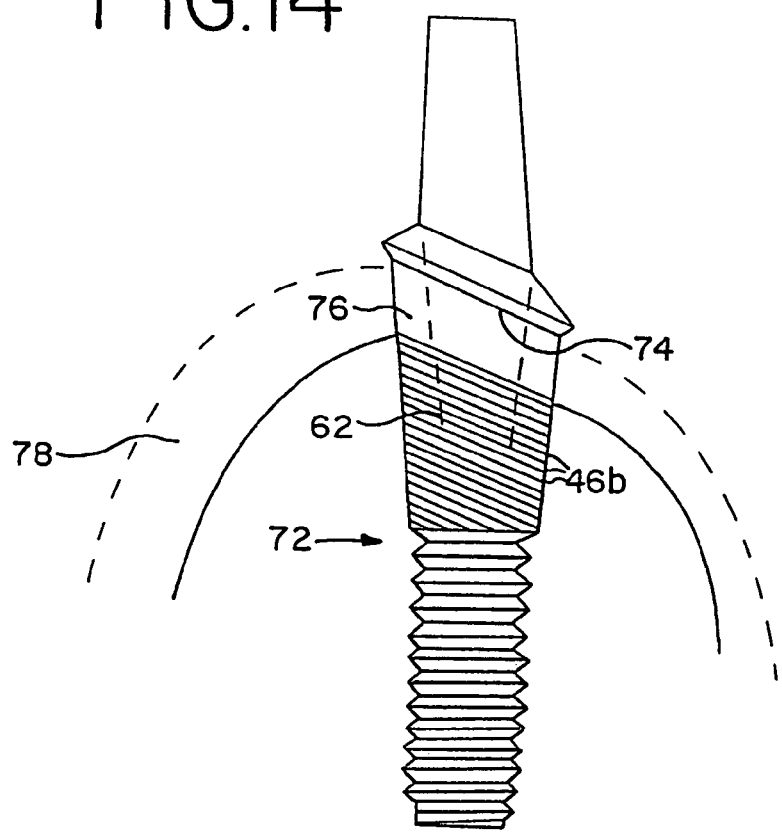
FIG. 14 is a side view of the preferred embodiment of the implant of the present invention of the single stage type configured to be used with snap-on impression caps.

FIG. 14, unlike FIGS. 6-12, illustrates a design of the present invention as it relates to a single stage type implant. This implant 72 also incorporates the sloped coronal 74 contours of the aforementioned designs. All advantages that apply to the two stage implant design apply to this design as well. A machined collar 76 coronal to the micro threads 46b and/or the textured surface 62 does not engage bone (the non-bone engaging surface of the implant) and passes through the soft tissue 78. This design allows for snap on impression caps (as described above) deemed essential to single stage designs. The perfect alignment afforded to the implants of FIGS. 13 and 14, due to the sloping coronal 52, provide for the perfect environment for snap-on impression caps.

Whether utilizing a single stage or a two-stage type implant, the basic methodology for the surgeon remains the same. First, the implant site is chosen. Next, taking into account the chosen site, the physical design for the shape and size for the implant is chosen. This is dependent upon the remaining jawbone shape and size as well as other factors. This design will include overall length as well as coronal differential, among others. Now, the surgeon positions the implant within the bone.

The present invention provides for more latitude to the surgeon with respect to placement of these implants. For example, single implants placed in the esthetic zone (upper anterior) will be much more predictable in outcome since soft tissue supporting bone mesial and distal of the implant body is preserved since bone on the lingual aspect of the fixture is not sacrificed or compromised. Similarly, the fixture design allows multiple implants to be placed in the esthetic zone, including implants placed next to one another. Since inter-implant bone is essentially preserved by the height of the lingual bone which is not sacrificed or compromised, papilla are maintained in the spaces between final implant supported restorations.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A dental implant system for implanting within a human jawbone, the implant comprising:
    a generally cylindrical one piece longitudinal body integrally formed as one piece having a lingual side, a buccal side and an outer surface, wherein said body has a length, an apical end on a lower portion, and a coronal end on an upper portion, the coronal end having an inner female conical shape that defines a cavity such that the height of the cavity is greatest on the lingual side and least on the buccal side that extends from the lingual side to the buccal side in a straight line; and
    an abutment with a connection portion having an outer male conical shape for connecting with said inner conical shape wherein said body has a varying height such that when said implant is positioned within the jawbone, the height is greatest on the lingual side and least on the buccal side;
    wherein said coronal end has a smooth convex contour such that said length is greatest on a generally lingual side and least on a generally buccal side.

2. The dental implant of claim 1, wherein said body is circular.

3. The dental implant of claim 1, further comprising a circumferentially oriented texture surface near said coronal end.

4. The dental implant of claim 3, wherein said circumferentially oriented texture surface comprises circumferential grooves.

5. The dental implant of claim 3, wherein said circumferentially oriented texture surface comprises micro-threads.

6. The dental implant of claim 5, wherein said micro-threads have multiple starting points.

7. The dental implant of claim 5, further comprising threads near said apical end.

8. The dental implant of claim 7, wherein said threads are larger than said micro-threads.

9. The dental implant of claim 7, wherein said threads are deeper than said micro-threads.

10. The dental implant of claim 5, wherein said micro-threads are bone engaging micro-threads.

* * * * *